United States Patent
Kim et al.

(10) Patent No.: US 10,126,223 B2
(45) Date of Patent: Nov. 13, 2018

(54) PARTICULATE MATTER SENSOR UNIT

(71) Applicant: Hyundai Motor Company, Seoul (KR)

(72) Inventors: Dong Gu Kim, Gyeonggi-do (KR); Sang Hyeok Yang, Gyeonggi-do (KR)

(73) Assignee: Hyundai Motor Company, Seoul (KR)

(*) Notice: Subject to any disclaimer, the term of this patent is extended or adjusted under 35 U.S.C. 154(b) by 107 days.

(21) Appl. No.: 15/259,514

(22) Filed: Sep. 8, 2016

(65) Prior Publication Data

US 2017/0299488 A1    Oct. 19, 2017

(30) Foreign Application Priority Data

Apr. 18, 2016 (KR) .......... 10-2016-0047080

(51) Int. Cl.
| | | |
|---|---|---|
| *G01N 15/06* | (2006.01) | |
| *F01N 11/00* | (2006.01) | |
| *G01N 15/10* | (2006.01) | |
| *F01N 13/00* | (2010.01) | |
| *G01N 27/22* | (2006.01) | |
| *G01N 15/00* | (2006.01) | |

(52) U.S. Cl.
CPC ....... *G01N 15/0618* (2013.01); *F01N 11/007* (2013.01); *F01N 13/008* (2013.01); *G01N 15/0606* (2013.01); *G01N 15/0656* (2013.01); *G01N 15/1031* (2013.01); *F01N 2560/05* (2013.01); *F01N 2560/06* (2013.01); *F01N 2560/20* (2013.01); *G01N 27/226* (2013.01); *G01N 2015/0046* (2013.01)

(58) Field of Classification Search
CPC ............ F01N 2560/05; G01N 15/1031; G01N 15/0618
USPC ................................. 73/23.31–23.33
See application file for complete search history.

(56) References Cited

U.S. PATENT DOCUMENTS

| 4,823,602 A | * | 4/1989 | Christensen, Jr. ..... G01H 11/06 73/661 |
| 5,627,306 A | * | 5/1997 | Yamauchi .......... G01N 27/4071 204/424 |

(Continued)

FOREIGN PATENT DOCUMENTS

| JP | 2006-170021 A | 6/2006 |
| JP | 2011-242148 A | 12/2011 |

(Continued)

*Primary Examiner* — John Fitzgerald
(74) *Attorney, Agent, or Firm* — Mintz Levin Cohn Ferris Glovsky and Popeo, P.C.; Peter F. Corless

(57) ABSTRACT

A particulate matter sensor unit is configured to sense particulate matter included in exhaust gas of a vehicle. The particulate matter sensor unit includes: a sensing unit sensing the particulate matter in the exhaust gas; a holding unit including a plurality of holders covering an exterior of the sensing unit, a front outer surface of each holder being formed by a tapered inclination outer surface; a shell having a hollow portion therein so that the holding unit is inserted and fitted into the shell, an inclination inner surface being formed in the hollow portion to correspond to the inclination outer surface; a cap unit installed in front of the shell to cover a sensing body of the sensing unit and guiding a flow of the exhaust gas to go through the sensing body; and a cover fixed to a rear end of the shell to support the holding unit.

9 Claims, 3 Drawing Sheets

(56) References Cited

U.S. PATENT DOCUMENTS

| | | | | |
|---|---|---|---|---|
| 5,922,938 A * | 7/1999 | Hafele | ............... | F01N 13/008 204/426 |
| 6,082,175 A * | 7/2000 | Yoshikawa | ............... | G01N 27/407 204/426 |
| 6,487,890 B1 * | 12/2002 | Weyl | ............... | G01N 27/4077 73/23.31 |
| 6,672,136 B2 * | 1/2004 | Kojima | ............... | G01N 27/4071 204/424 |
| 7,306,708 B2 * | 12/2007 | Okuno | ............... | G01N 27/4071 204/425 |
| 7,589,280 B2 * | 9/2009 | Nelson | ............... | G01D 11/245 174/84 C |
| 7,980,132 B2 * | 7/2011 | Gustin | ............... | G01N 27/4077 73/23.31 |
| 8,047,051 B2 * | 11/2011 | McCauley | ............... | G01N 27/4078 73/23.31 |
| 8,278,907 B2 * | 10/2012 | Sakuma | ............... | G01N 15/0656 324/71.4 |
| 8,419,915 B2 * | 4/2013 | Furuta | ............... | G01N 27/4071 204/424 |
| 8,591,104 B2 * | 11/2013 | Suzuki | ............... | B23K 26/127 374/163 |
| 8,591,712 B2 * | 11/2013 | Hayashi | ............... | G01N 27/4071 204/424 |
| 8,707,761 B2 * | 4/2014 | Maeda | ............... | G01N 15/0656 73/23.33 |
| 8,771,488 B2 * | 7/2014 | Ito | ............... | G01N 27/406 204/424 |
| 8,852,415 B2 * | 10/2014 | Runge | ............... | G01N 27/4072 204/424 |
| 8,860,439 B2 * | 10/2014 | Kimata | ............... | F01N 11/00 324/464 |
| 2005/0155408 A1 * | 7/2005 | Weyl | ............... | G01K 1/14 73/23.31 |
| 2006/0288806 A1 * | 12/2006 | Nelson | ............... | G01D 11/245 73/866.5 |
| 2007/0056353 A1 * | 3/2007 | Weyl | ............... | G01N 27/4077 73/23.31 |
| 2007/0158191 A1 * | 7/2007 | Berger | ............... | G01N 15/0656 204/421 |
| 2008/0271518 A1 * | 11/2008 | Treutler | ............... | G01N 27/4062 73/23.31 |
| 2010/0031733 A1 * | 2/2010 | Bollinger | ............... | F02D 41/1466 73/28.04 |
| 2010/0050738 A1 * | 3/2010 | Gustin | ............... | G01N 27/4077 73/23.31 |
| 2011/0209523 A1 * | 9/2011 | Otsubo | ............... | G01N 27/4077 73/23.31 |
| 2012/0006093 A1 * | 1/2012 | Yamada | ............... | G01N 27/4078 73/23.31 |
| 2012/0073356 A1 * | 3/2012 | Nishijima | ............... | G01N 27/4075 73/23.32 |
| 2012/0085146 A1 * | 4/2012 | Maeda | ............... | G01N 27/043 73/23.31 |
| 2012/0103057 A1 * | 5/2012 | Kimata | ............... | G01N 15/0656 73/23.33 |
| 2012/0103058 A1 * | 5/2012 | Maeda | ............... | G01N 15/0656 73/23.33 |
| 2012/0118086 A1 * | 5/2012 | Horn | ............... | G01D 11/245 73/866.5 |
| 2012/0324981 A1 * | 12/2012 | Hedayat | ............... | G01N 15/0656 73/23.33 |
| 2014/0260531 A1 * | 9/2014 | Oba | ............... | G01N 27/4078 73/23.2 |
| 2014/0338424 A1 * | 11/2014 | Kume | ............... | G01M 15/102 73/31.05 |
| 2015/0114085 A1 * | 4/2015 | Iwano | ............... | G01N 27/409 73/23.32 |
| 2015/0168285 A1 * | 6/2015 | Hedayat | ............... | G01M 15/102 73/23.33 |
| 2016/0139071 A1 * | 5/2016 | Nakano | ............... | F02M 35/10386 73/23.31 |
| 2017/0211454 A1 * | 7/2017 | Matsuoka | ............... | F01N 11/007 |

FOREIGN PATENT DOCUMENTS

| | | |
|---|---|---|
| JP | 2012-093287 A | 5/2012 |
| JP | 2012-146449 A | 8/2012 |
| JP | 2012-233874 A | 11/2012 |
| KR | 10-0893371 | 8/2008 |
| KR | 10-1243645 | 2/2011 |

* cited by examiner

PARTICULATE MATTER SENSOR UNIT

CROSS-REFERENCE TO RELATED APPLICATION

This application claims under 35 U.S.C. § 119(a) the benefit of Korean Patent Application No. 10-2016-0047080 filed in the Korean Intellectual Property Office on Apr. 18, 2016, the entire contents of which are incorporated herein by reference.

BACKGROUND (a) Technical Field

The present invention relates to a particulate matter sensor unit, and more particularly, to a particulate matter sensor unit which can simplify a combination process through mechanical packaging.

(b) Description of the Related Art

In recent years, with additional exhaust gas regulations applicable to a vehicle, a concern about a post-processing device that purifies exhaust gas has increased.

In particular, a diesel engine vehicle generates an exhaust flow including a variable amount of particulate matter (PM), which is known as a primary cause of atmospheric pollution, and as a result, regulations applicable to vehicle exhaust of a diesel vehicle have become more strict.

A diesel particulate filter (DPF) is applied to an exhaust line in order to reduce particulate matter of the diesel vehicle, and a particulate matter sensor unit is applied in order to sense the amount of exhaust gas collected in the DPF.

The particulate matter sensor unit is a device that detects a change in resistance or capacitance, which occurs as the particulate matter included in the exhaust gas is accumulated in a sensing unit, and is installed on a rear stage of the DPF in the exhaust line.

In the particulate matter sensor unit, the sensing unit is fixed onto a substrate through a joining body and processes a via hole to be electrically connected, while packaging.

In this case, the adhesive body generally adopts an adhesive body which is made of silver (Ag).

However, the particulate matter sensor unit in the related art has a problem in that processes such as forming the joining body in order to fix the substrate and the sensing unit, processing the via hole for the electrical connection, and the like while packaging are complicated.

The above information disclosed in this Background section is only for enhancement of understanding of the background of the invention and therefore it may contain information that does not form the prior art that is already known in this country to a person of ordinary skill in the art.

SUMMARY

The preset invention provides a particulate matter sensor unit which has a simple combination structure by mechanically packaging a sensing body interposed in a holder device by cam actuation of an inclination inner surface formed on an inner surface of a shell and an inclination outer surface formed on an outer surface of the holder device through mutual contact of the inclination inner and outer surfaces.

An exemplary embodiment of the present invention provides a particulate matter sensor unit configured to sense a particulate matter included in exhaust gas of a vehicle, including: a sensing unit sensing the particulate matter in the exhaust gas a holding unit including a plurality of holders covering an exterior of the sensing unit, a front outer surface of each holder being formed by a tapered inclination outer surface; a shell having a hollow portion therein so that the holding unit is inserted and fitted into the shell, an inclination inner surface being formed in the hollow portion to correspond to the inclination outer surface; a cap unit installed in front of the shell to cover a sensing body of the sensing unit and guiding a flow of the exhaust gas to go through the sensing body; and a cover fixed to a rear end of the shell to support the holding unit and having a terminal through-hole at a center of the cover.

The sensing unit may include a sensing body sensing the particulate matter as a capacitance value varies when the particulate matter is collected; an upper substrate positioned above the sensing body, having an upper fixation groove, and having a measurement hole penetrably formed on the upper fixing groove so that a predetermined part of the sensing body is exposed; and a lower substrate positioned below the sensing body and having a lower fixation groove.

The sensing body may be fixed to the fixation grooves formed in the upper substrate and the lower substrate, respectively, and as a result, a part of the sensing body is exposed through the measurement hole.

In the upper substrate, a contact contacting an electrode of the sensing body may be formed on the inner surface of the fixation groove and the contact may be connected with electrode pads disposed on one surface and another surface of the upper substrate through an electrode pattern formed on the upper substrate.

The upper substrate may have a larger length than the lower substrate and protrude to the outside of a cover through the terminal through-hole to be electrically connected with a terminal through each electrode pad.

The sensing body may include a sensing substrate; a heater electrode formed on the sensing substrate in a predetermined pattern to bum and remove the collected particulate matter; a temperature sensor formed along an edge of the heater electrode on the sensing substrate in a predetermined pattern and sensing a temperature; and a measurement electrode installed in insulating layer formed above the temperature sensor and the heater electrode and having the capacitance value which varies by the collected particulate matter.

In the holding unit, a front outer surface of the holding unit may have a conical shape while two holders in which a rear side is formed by a semicircular cross-section and a front outer surface may be formed by the tapered inclination outer surface are combined.

The two holders may include an upper holder having an upper support groove formed in a longitudinal direction so that the upper substrate of the sensing unit is seated; and a lower holder having a lower support groove formed for a predetermined section in the longitudinal direction so that the lower substrate of the sensing unit is seated.

The shell may include a cap installation end having the front in the cap unit is fitted; an exhaust line fastening end formed at the rear side of the cap installation end and having a screw tab on the outer periphery thereof so as to be fastened with the exhaust line; a tool application end formed by a polygonal cross-section at the rear side of the exhaust line fastening end; and a cover installation end formed at the rear side of the tool application end and having the screw tab formed on the outer periphery thereof so as to fasten the cover.

The cap unit may include an internal cap having a receiving part therein so as to cover the sensing body; and an external cap covering the exterior of the internal cap, a fixation end for fixing the sensing body to the shell is formed on a rear end of the internal cap, a discharge hole may be formed at the center of the front of the internal cap, and an intake hole may be formed in a part where the fixation end and the internal cap may be connected at a predetermined interval, and the rear end of the external cap may be fitted in a step surface of the fixation end and an exhaust gas inflow passage may be formed between the outer surface of the internal cap and the inner surface of the external cap so that external exhaust gas flows in to move the intake hole.

According to an exemplary embodiment of the present invention, while a sensing body sensing a particulate matter is interposed by a holder device to be inserted into a shell, an inclination inner surface formed on the inner surface of the shell and an inclination outer surface formed on the outer surface of the holder device contact each other to achieve cam actuation, and as a result, a particulate matter sensor unit may be combined in a simple structure.

Besides, an effect which can be obtained or predicted by the exemplary embodiment of the present invention is directly or implicitly disclosed in detailed description of the exemplary embodiment of the present invention. That is, various effects predicted according to the exemplary embodiment of the present invention will be disclosed in the detailed description to be described below.

DETAILED DESCRIPTION OF THE EMBODIMENTS

Figure 1:
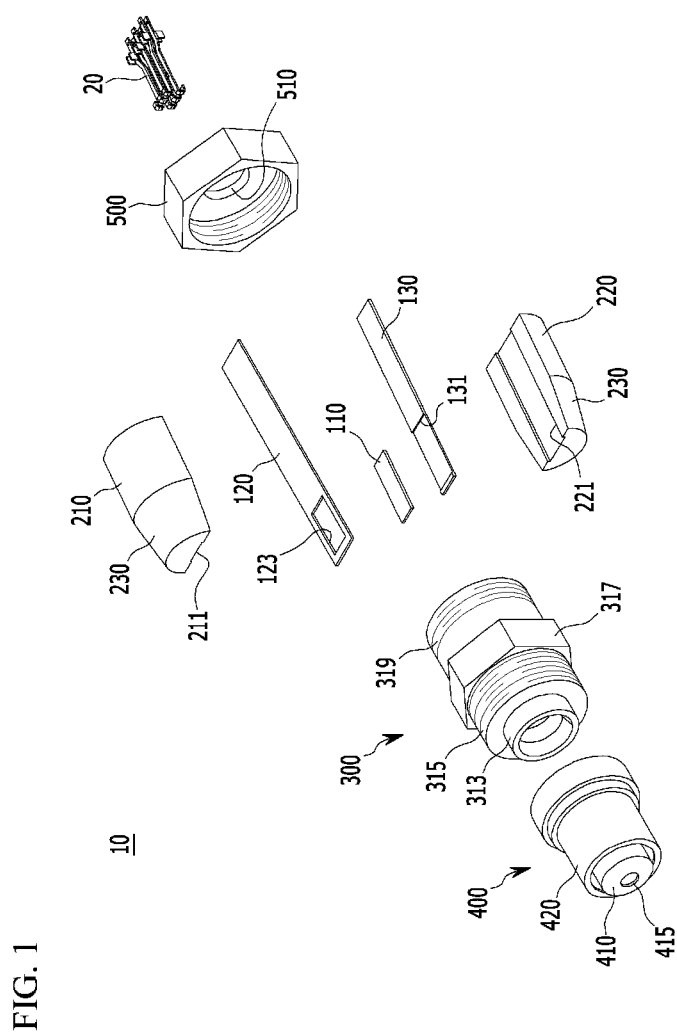
FIG. 1 is an exploded perspective view of a particulate matter sensor unit according to an exemplary embodiment of the present invention.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Throughout the specification, unless explicitly described to the contrary, the word "comprise" and variations such as "comprises" or "comprising" will be understood to imply the inclusion of stated elements but not the exclusion of any other elements. In addition, the terms "unit", "-er", "-or", and "module" described in the specification mean units for processing at least one function and operation, and can be implemented by hardware components or software components and combinations thereof.

Further, the control logic of the present invention may be embodied as non-transitory computer readable media on a computer readable medium containing executable program instructions executed by a processor, controller or the like. Examples of computer readable media include, but are not limited to, ROM, RAM, compact disc (CD)-ROMs, magnetic tapes, floppy disks, flash drives, smart cards and optical data storage devices. The computer readable medium can also be distributed in network coupled computer systems so that the computer readable media is stored and executed in a distributed fashion, e.g., by a telematics server or a Controller Area Network (CAN).

Hereinafter, an exemplary embodiment of the present invention will be described with reference to the accompanying drawings. However, drawings illustrated below and detailed description to be described below are related to one preferred embodiment among various exemplary embodiments for effectively describing a feature of the present invention. Accordingly, the present invention should not be limited only to the drawings and description given below.

Figure 2:
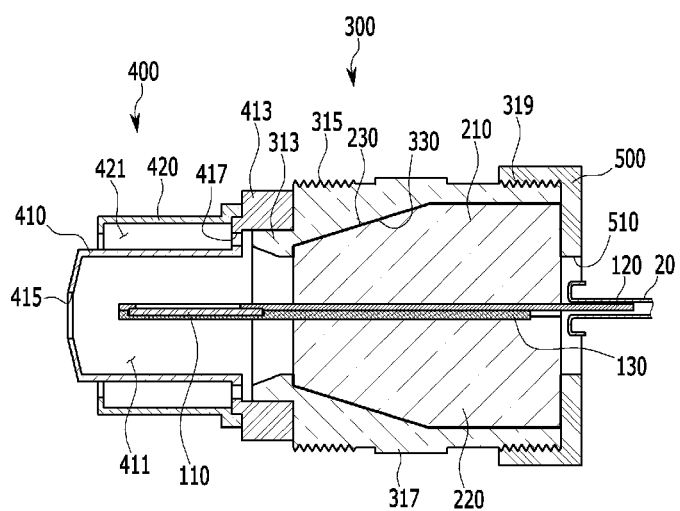
FIG. 2 is a cross-sectional view of the particulate matter sensor unit according to the exemplary embodiment of the present invention.
Figure 3:
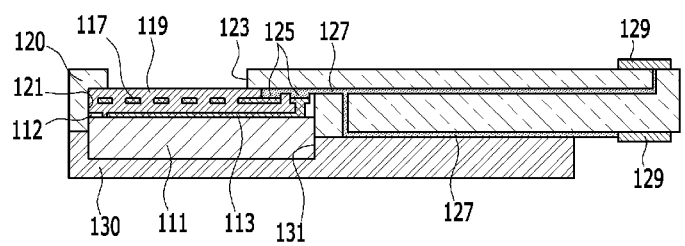
FIG. 3 is a cross-sectional view of a sensing body of the particulate matter sensor unit according to the exemplary embodiment of the present invention.

FIG. 1 is an exploded perspective view of a particulate matter sensor unit according to an exemplary embodiment of the present invention, and FIG. 2 is a cross-sectional view of the particulate matter sensor unit according to the exemplary embodiment of the present invention.

Exhaust gas flows in an exhaust line of a vehicle, and the exhaust gas includes particulate matter.

The particulate matter sensor unit according to the exemplary embodiment of the present invention is disposed on the exhaust line to sense the particulate matter included in the exhaust gas.

Referring to FIGS. 1 and 2, the particulate matter sensor unit 10 includes a sensing unit 100, a holding unit 200, a shell 300, a cap unit 400, and a cover 500.

The sensing unit 100 includes a sensing body 110, an upper substrate 120, and a lower substrate 130, and the sensing unit 100 senses the particulate matter included in the exhaust gas through the sensing body 110 fixed to fixation grooves 121 and 131 formed in the upper substrate 120 and the lower substrate 130, respectively.

In particular, the sensing body 110 senses the particulate matter as a capacitance value varies when the particulate matter in the exhaust gas is collected.

The sensing body 110 includes a sensing substrate 111, a heater electrode 113, a temperature sensor 112, and a measurement electrode 117.

The sensing body 110 includes a heater electrode 113 which is formed on the sensing substrate 111 in a predetermined pattern and burns and removes the collected particulate matter, a temperature sensor 112 that is formed on the sensing substrate 111 in a predetermined pattern along an edge of the heater electrode 113 sensing a temperature, and the measurement electrode 117 formed in an insulating layer 119 formed above the temperature sensor 112 and the heater electrode 113 and having the capacitance value which varies by the collected particulate matter.

The sensing body 110 may be formed by micro electro mechanical system (MEMS) technology.

In addition, the upper substrate 120 is positioned on the top of the sensing body 110, and an upper fixation groove 121 is formed on one surface of the upper substrate 120.

A measurement hole 123 is penetrably formed to penetrate on the upper fixation groove 121 of the upper substrate 120 so that a predetermined part of the sensing body 110 is exposed.

Further, in the upper substrate 120, a contact 125 that contacts an electrode of the sensing body 110 is formed on the inner surface of the upper fixation groove 121.

The contact 125 is mutually connected with an electrode pad 129 configured on one surface and another surface of a fore end of the upper substrate 120 through an electrode pattern 127 formed in the inside and on one surface of the upper substrate 120.

The upper substrate 120 has a larger length than the lower substrate 130 and the upper substrate 120 protrudes on an exterior of the cover 500 through a terminal through-hole 510 formed in the cover 500 to be electrically connected with a terminal 20 through each electrode pad 129.

In addition, the lower substrate 130 is positioned below the sensing body 110, and a lower fixation groove 131 is formed on one surface corresponding to one surface of the upper substrate 120.

Meanwhile, the holding unit 200 includes a plurality of holders covering exteriors of the upper substrate 120 and the lower substrate 130 of the sensing unit 100.

In the holding unit 200, a front outer surface of each holder is formed by a tapered inclination outer surface 230.

That is, in the holding unit 200, rear sides of two holders are formed by a semicircular cross-section and the two holders are combined, where a front outer surface of the holding unit 200 has a conical shape.

For example, the two holders are constituted by an upper holder 210 and a lower holder 220.

An upper support groove 211 is formed in the upper holder 210 in a longitudinal direction so that the upper substrate 120 is seated.

Further, a lower support groove 221 is formed in the lower holder 220 in the longitudinal direction for a predetermined section so that the lower substrate 130 is seated.

In addition, a hollow portion is formed in the shell 300 so that the holding unit 200 is inserted and fitted into the shell 300.

Moreover, an inclination inner surface 330 is formed in the hollow portion of the shell 300 to correspond to the inclination outer surface 230 of the holding unit 200.

The shell 300 includes a cap installation end 313, an exhaust line fastening end 315, a tool application end 317, and a cover installation end 319.

First, the cap unit 400 is fitted in front of the cap installation end 313.

Further, a screw tab is formed on the outer periphery so that the exhaust line fastening end 315 is formed at a rear side of the cap installation end 313 to be fastened with the exhaust line.

In addition, the tool application end 317 is formed by a polygonal cross-section at the rear side of the exhaust line fastening end 315.

A shape of the tool application end 315 may be changed to correspond to a tool used for assembling the particulate matter sensor unit 10 to the exhaust line.

Further, the cover installation end 319 is formed at the rear side of the tool application end 317, and the screw tab is formed on the outer periphery so that the cover 500 is fastened.

In addition, the cap unit 400 is installed in front of the shell 300 and is formed to cover the sensing body 110 of the sensing unit 100 to guide the exhaust gas in the exhaust line so that the flow of exhaust gas in the exhaust line goes through the sensing body 110.

The cap unit 400 includes an internal cap 410 and an external cap 420.

A receiving part 411 is formed in the internal cap 410 so as to cover the sensing body 110, and a fixation end 413 for fixing the sensing body 110 to the shell 300 is integrally formed at a rear end of the internal cap 410.

Further, a discharge hole 415 is formed at the center of the front of the internal cap 410, and a plurality of intake holes 417 is formed in a part where the internal cap 410 and the fixation end 413 are connected to each other at a predetermined interval.

In addition, a rear end of the external cap 420 is fitted in a step surface of the fixation end 413, and as a result, the external cap 420 is installed while covering an exterior of the internal cap 410.

An exhaust gas inflow passage 421 is formed in the external cap 420 so that external exhaust gas flows between the external cap 420 and the outer surface of the internal cap 410 to be guided into the intake hole 417.

The cover 500 is fixed to a rear end of the shell 300 to support the holding unit 200 and the terminal through-hole 510 is formed at the center of the cover 500.

The cover 500 is fastened to the cover installation end 319 formed on the rear end of the shell 300.

Therefore, in the particulate matter sensor unit 10 according to the exemplary embodiment of the present invention, the sensing body 110 is fitted between the fixation grooves 121 and 131 of the upper substrate 120 and the lower substrate 130, respectively, and the sensing body 110 is fitted in the shell 300 while being fixed through the support grooves 211 and 221 of the upper holder 210 and the lower holder 220, respectively, and as a result, the sensing body 110 is pressed in and combined by using the cover 500 while the inclination outer surfaces 230 of the upper holder 210 and the lower holder 220 contact the inclination inner surface 330 of the shell 300.

In this case, the sensing body 110 is exposed to the front of the shell 300, and the upper holder 210 is exposed to the outside through the terminal through-hole 510 of the cover 500 to be electrically connected with the terminal 20.

Further, the sensing body 110 is protected through the cap unit 400 installed in front of the shell 300.

In addition, the exhaust gas flows through the exhaust gas inflow passage 421 and the intake hole 417 formed in the cap unit 400 and discharged to the discharge hole 415 through the sensing body 110.

As a result, in the particulate matter sensor unit 100 according to the exemplary embodiment of the present invention, the inclination outer surface 230 of the holding unit 200 and the inclination inner surface 330 of the shell 300 contact each other to perform the cam actuation, and as a result, the particulate matter sensor unit 10 is assembled, thus providing a simple mechanical packaging structure.

Further, the particulate matter sensor unit 100 according to the exemplary embodiment of the present invention can secure bonding reliability even under a high-temperature condition by driving the heater electrode 113.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A particulate matter sensor unit configured to sense a particulate matter included in exhaust gas of a vehicle, comprising:
   a sensing unit including a sensing body sensing the particulate matter in the exhaust gas;
   a holding unit including a plurality of holders covering an exterior of the sensing unit, each holder including a tapered inclination outer surface;
   a shell having a hollow portion therein so that the holding unit is inserted and fitted into the shell, an inclination inner surface being formed in the hollow portion to correspond to the inclination outer surface;
   a cap unit arranged to cover the sensing body of the sensing unit; and
   a cover fixed to the shell to support the holding unit and having a terminal through-hole at a center of the cover, wherein the cap unit includes:
      an internal cap having a front end and a rear end, and a receiving part therein so as to cover the sensing body; and
      an external cap covering the internal cap,
      a fixation end formed at the rear end of the internal cap for fixing the sensing body to the shell,
      a discharge hole being formed in the front end of the internal cap,
      a plurality of intake holes being formed at a predetermined interval in a part where the fixation end and the internal cap are connected,
      the external cap configured to be fitted to the fixation end of the cap unit via a step surface, and
      an exhaust gas inflow passage being formed between an outer surface of the internal cap and an inner surface of the external cap to allow external exhaust gas to flow through the intake hole.

2. The particulate matter sensor unit of claim 1, wherein the shell includes:
   a cap installation end;
   an exhaust line fastening end formed at the cap installation end and having a screw tab on an outer periphery thereof so as to be fastened with the exhaust line;
   a tool application end formed by a polygonal cross-section at the exhaust line fastening end; and
   a cover installation end formed at the tool application end and having the screw tab formed on the outer periphery thereof so as to fasten the cover.

3. The particulate matter sensor unit of claim 1, wherein the sensing body includes:
   a sensing substrate;
   a heater electrode formed on the sensing substrate in a predetermined pattern to burn and remove the collected particulate matter;
   a temperature sensor formed along an edge of the heater electrode on the sensing substrate for sensing a temperature; and
   a measurement electrode installed in an insulating layer and having a capacitance value which varies by the collected particulate matter.

4. The particulate matter sensor unit of claim 1, wherein an outer surface of the holding unit has a conical shape, and two of the holders are configured to be combined.

5. The particulate matter sensor unit of claim 4, wherein the two holders include:
   an upper holder having an upper support groove formed in a longitudinal direction so that the upper substrate of the sensing unit is seated; and
   a lower holder having a lower support groove formed for a predetermined section in the longitudinal direction so that the lower substrate of the sensing unit is seated.

6. The particulate matter sensor unit of claim 1, wherein the sensing unit includes:
   a sensing body sensing the particulate matter as a capacitance value varies when the particulate matter is collected;
   an upper substrate positioned above the sensing body, having an upper fixation groove, and having a measurement hole penetrably formed on the upper fixation groove so that a predetermined part of the sensing body is exposed; and
   a lower substrate positioned below the sensing body and having a lower fixation groove.

7. The particulate matter sensor unit of claim 6, wherein the sensing body is fixed to the upper and lower fixation grooves formed in the upper substrate and the lower substrate, respectively, and as a result, a part of the sensing body is exposed through the measurement hole.

8. The particulate matter sensor unit of claim 6, wherein in the upper substrate, a contact contacting an electrode of the sensing body is formed in the upper fixation groove, and the contact is connected with electrode pads disposed on the upper substrate.

9. The particulate matter sensor unit of claim 8, wherein the upper substrate is longer than the lower substrate and protrudes to an outside of the cover through the terminal through-hole to be electrically connected with a terminal through each of the electrode pads.

* * * * *